United States Patent [19]

Dschen

[11] Patent Number: 5,231,462

[45] Date of Patent: Jul. 27, 1993

[54] OPTICAL SPECTROPHOTOMETER WITH WAVELENGTH MODULATION

[75] Inventor: Tsing Dschen, Dietikon, Switzerland

[73] Assignee: Landis & Gyr Betriebs AG, Zug, Switzerland

[21] Appl. No.: 840,863

[22] Filed: Feb. 25, 1992

[30] Foreign Application Priority Data

Mar. 4, 1991 [CH] Switzerland ............ 00644/91

[51] Int. Cl.⁵ .................... G01J 3/06; G01J 3/18; G01J 3/26
[52] U.S. Cl. ......................... 356/328; 356/334; 356/346; 356/352
[58] Field of Search ............ 356/308, 309, 319, 323, 356/325, 326, 328, 331, 332, 334, 346, 352

[56] References Cited

U.S. PATENT DOCUMENTS

| | | | |
|---|---|---|---|
| 3,565,567 | 2/1971 | Rains | 356/315 |
| 3,832,558 | 8/1974 | Fern et al. | 250/461.1 |
| 4,051,371 | 9/1977 | Dewey, Jr. | 250/339 |

FOREIGN PATENT DOCUMENTS

| | | |
|---|---|---|
| 2148492 | 5/1985 | United Kingdom . |
| 2169418 | 7/1986 | United Kingdom . |
| 2181536 | 4/1987 | United Kingdom . |

OTHER PUBLICATIONS

Hieftje et al, Applied Spectroscopy, vol. 26, No. 6 Nov./Dec. 1972, pp. 624-631.
T. Izumi et al, "Repetitive-scanning Derivative spectrometer as a monitor of environmental air pollution," Applied Optics, vol. 22, No. 22 Nov. 15, 1983.

*Primary Examiner*—F. L. Evans
*Attorney, Agent, or Firm*—Marmorek, Guttman & Rubenstein

[57] ABSTRACT

A spectrophotometer useful for measuring absorption or emission bands of a substance irradiated with optical radiation, comprises a light source for producing the optical radiation, a monochromator for isolating light of wavelength (W) from the optical radiation and which modulates the wavelength (W) by a predetermined wavelength amplitude ($\delta W$), and a photodetector for detecting the intensity of light passing through the monochromator and for producing a measuring signal in response thereto. The monochromator operates under the control of an electronic control unit which produces a control signal that causes the monochromator to scan across a portion of the spectrum of the optical radiation at a frequency ($f_2$) to transmit a narrow band of radiation at the wavelength (W). The control unit includes a modulation generator which produces a signal that causes the monochromator to modulate the wavelength (W) by the predetermined wavelength amplitude ($\delta W$) at a frequency ($f_1$). The spectrophotometer also includes an electronic evaluation unit which amplifies an a.c. component of the measuring signal that is attributable to the wavelength modulation in synchronization with the signal produced by the modulation generator. In one preferred embodiment, the monochromator comprises a diffraction grating and a drive unit which causes the diffraction to rotate about a pivot axis and which superimposes an oscillatory motion on the rotational movement. In another preferred embodiment, the monochromator comprises a Fabry-Perot resonator and a drive unit which adjusts the optical length of the Fabry-Perot resonator under the control of the control unit.

13 Claims, 2 Drawing Sheets

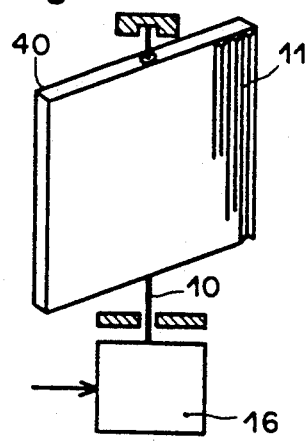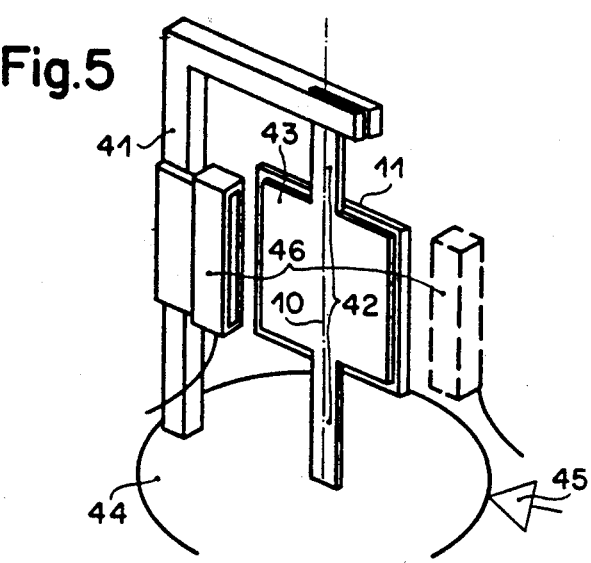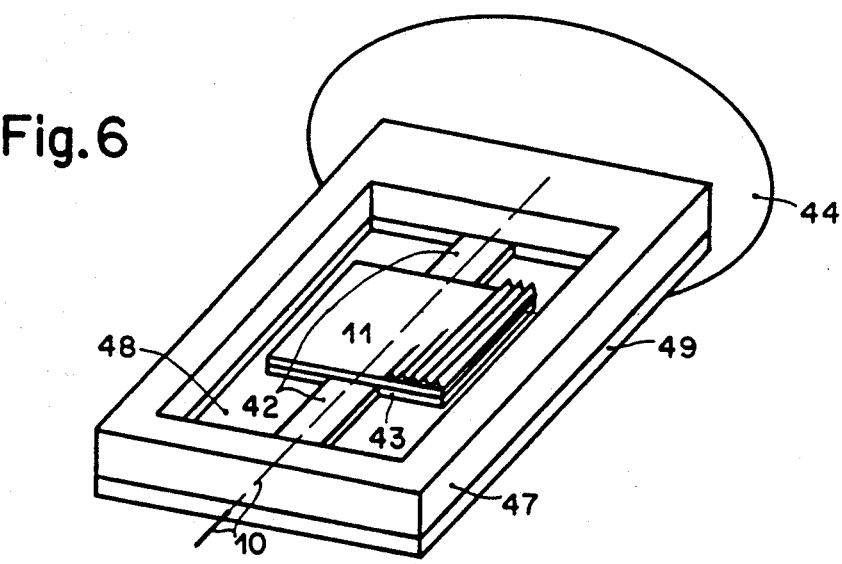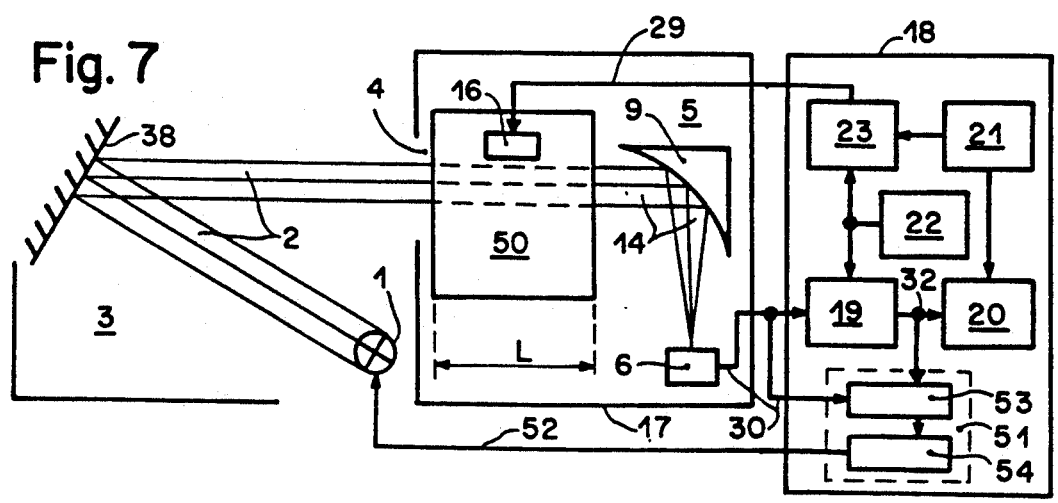

OPTICAL SPECTROPHOTOMETER WITH WAVELENGTH MODULATION

BACKGROUND OF THE INVENTION

The instant invention relates to an optical spectrophotometer having a light source which emits optical radiation (IR, visible, and UV), and a monochromator which isolates narrow portions of the spectrum of the emitted light in order to measure the absorption or emission bands of a substance.

Such an optical spectrophotometer can be used to detect the presence of substances in a medium, in particular, to measure the concentration of pollutants in the air.

An optical spectrophotometer of this type is described in U.S. Pat. No. 4,732,476. It includes a monochromator provided with a diffraction grating which rotates around a predetermined axis at a constant angular velocity. When the diffraction grating is illuminated with white light, it produces in a testing chamber a monochromatic light ray having a wavelength which goes through the entire spectrum as a function of the position of the diffraction grating and of time. A photodetector is located after the testing chamber and measures the intensity of the spectrum altered by the absorption effect of substances which are present in the testing chamber.

Another spectrophotometer is known from U.S. Pat. No. 4,070,111 in which a diffraction grating is seated on the axle of a galvanometer. Filtered light, the wavelength of which scans back and forth across the spectrum of the light source, is broken up for analysis into a reference ray and into a measured ray passing through a testing chamber.

Further, GB-A 2,181,536 discloses an optical sensing arrangement in which a testing chamber for gaseous substances is irradiated with light coming from a white light source. The spectrum of the light which is altered by the substances present in the testing chamber is analyzed in a Fabry-Perot resonator which acts as a filter with a narrow bandwidth. The optical length of the Fabry-Perot resonator is varied periodically by means of an electric signal having an asymmetric saw-tooth configuration. During every period, the Fabry-Perot resonator is caused to scan a narrow portion of the spectrum that is determined by the electric signal. The thus-filtered light reaches the photodetector and produces an output signal which is evaluated as a function of the electric signal.

It is the object of the instant invention to provide an inexpensive optical spectrophotometer which is of simple construction and which makes it possible to amplify a measured signal with little noise.

SUMMARY OF THE INVENTION

This and other objects are achieved by means of a spectrophotometer useful for measuring absorption or emission bands of a substance irradiated with optical radiation, comprising a light source for producing the optical radiation, a monochromator for isolating light of wavelength (W) from the optical radiation and which modulates the wavelength (W) by a predetermined wavelength amplitude ($\delta W$), and a photodetector for detecting the intensity of light passing through the monochromator and for producing a measuring signal in response thereto. The monochromator operates under the control of an electronic control unit which produces a control signal that causes the monochromator to scan across a portion of the spectrum of the optical radiation at a frequency $f_2$ to transmit a narrow band of radiation at the wavelength (W). The control unit includes a modulation generator which produces a signal that causes the monochromator to modulate the wavelength (W) by the predetermined wavelength amplitude ($\delta W$) at a frequency ($f_1$). The spectrophotometer also includes an electronic evaluation unit which amplifies an a.c. component of the measuring signal that is attributable to the wavelength modulation in synchronization with the signal produced by the modulation generator.

In one preferred embodiment, the monochromator comprises a diffraction grating and a drive unit operating under the control of the control unit which causes the diffraction grating to rotate about a pivot axis and which superimposes an oscillation motion on the rotational movement. The rotational movement causes the monochromator to scan across a portion of the spectrum to transmit the light at wavelength (W), while the oscillations cause the wavelength modulation.

In another preferred embodiment, the monochromator comprises a Fabry-Perot resonator and a drive unit which adjusts the optical length of the Fabry-Perot resonator under the control of the control unit. Controlled adjustment of the optical length of the Fabry-Perot resonator causes the monochromator to scan across a portion of the spectrum to transmit radiation of wavelength (W) as well as to modulate the wavelength.

BRIEF DESCRIPTION OF THE DRAWINGS

Embodiments of the invention are explained in greater detail by reference to the drawings, wherein FIG. 4 shows a rotatable diffraction grating, FIG. 5 shows a diffraction grating with mountings, FIG. 6 shows a substrate with a diffraction grating suspended from mountings, and FIG. 7 shows a spectrophotometer with a Fabry-Perot resonator.

DETAILED DESCRIPTION OF THE INVENTION

Figure 1:
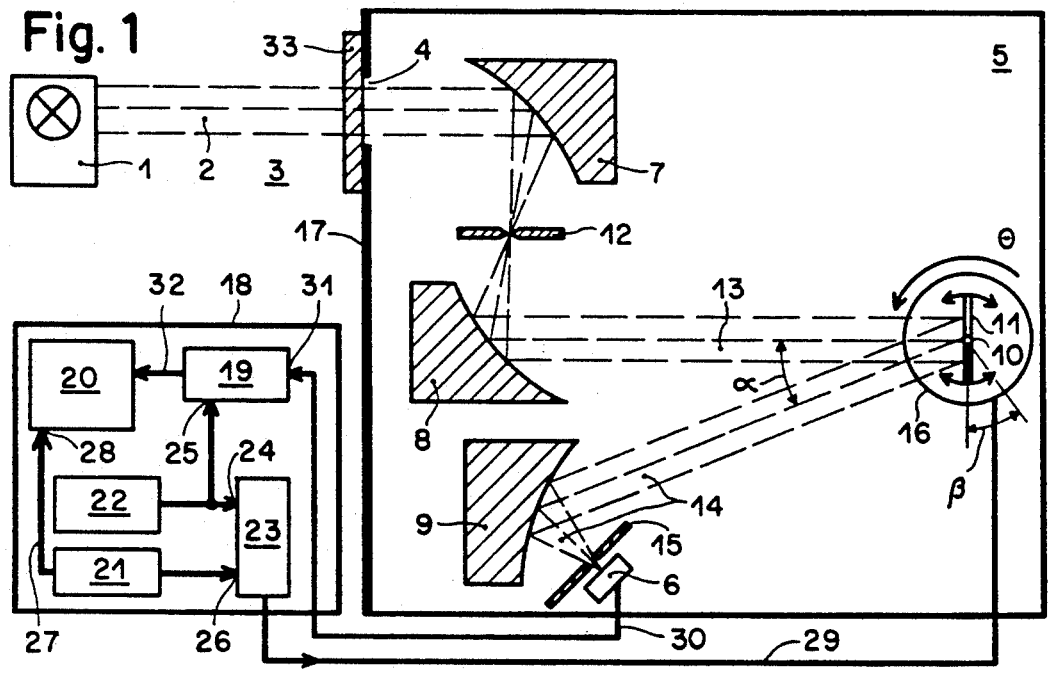
FIG. 1 shows a spectrophotometer having a diffraction grating.

In FIG. 1, the reference number 1 designates a light source producing wide-band electromagnetic radiation 2 which is transmitted, preferably along parallel rays, through a testing chamber 3 located between the light source 1 and a spectrophotometer. Substances, e.g., gases, present in the testing chamber 3 cause a spectral alteration of the radiation 2. Through an inlet opening 4, the radiation 2 enters a monochromator 5 of the spectrophotometer which acts as a narrow-band filter and allows only a predetermined wavelength W to pass through. A photodetector 6 located after the monochromator 5 produces an electric measuring signal.

Advantageously, the testing chamber 3 is located between the light source 1 and the inlet opening 4 so that its size is limited only by the intensity of the radiation 2. It is also possible to install the testing chamber 3 within or after the monochromator 5.

The monochromator 5 illustrated in FIG. 1 includes a focusing mirror system comprising an input mirror 7, a central mirror 8 and a focusing mirror 9. The monochromator 5 also includes a reflecting diffraction grating 11 rotatable around a pivot axis 10 which acts as a means for selecting a particular wavelength. In FIG. 1, the path of the rays in the spectrophotometer is indicated by broken lines. The radiation 2 entering through the inlet opening 4 is intercepted by the input mirror 7 and is focused into the opening of an input diaphragm 12. The central mirror 8 intercepts the radiation 2, which is divergent after the input diaphragm 12, and projects it as a bundle of parallel rays 13 onto the diffraction grating 11. The radiation 2 is spectrally resolved into different wavelengths by diffraction grating 11 and is reflected at a predetermined diffraction angle $\pm\alpha$ to the bundle 13. The focusing mirror 9 collects all the rays 14 diffracted by the diffraction grating 11 at an angle $+\alpha$ and projects them in its focal plane upon an output diaphragm 15 installed before the photodetector 6. Only the rays 14 having the wavelength W pass through an opening of the output diaphragm 15 and fall upon the photodetector 6.

The axis 10 is aligned so as to be parallel with the grating lines of the diffraction grating 11 and in FIG. 1 the axis is positioned at a right angle to the plane of the drawing. The diffraction grating 11 is connected directly to the axis 10, e.g., by bonding. The bundle 13 can fall perpendicularly on a plane containing the axis 10 for instance.

A driving means 16 is connected to the axis 10 and rotates the diffraction grating 11 around the axis 10 by an angle of rotation $\Theta$. The predetermined wavelength W is no longer diffracted by the diffraction angle $\pm\alpha$ but by an angle $\Theta\pm\alpha$ to the bundle 13, the angle $\Theta$ being measured starting at the bundle 13. However, since only those rays 14 which are diffracted by the angle $+\alpha$ determined by the mirror system pass through the output diaphragm 15 and fall upon the photodetector 6, the wavelength W of the radiation 2 recorded in the photodetector 6 changes with the rotational movement of the diffraction grating 11.

In addition to the rotational movement around the axis 10, the driving means 16 also produces an oscillating movement, e.g., a sinusoidal movement, of the diffraction grating 11 with an oscillatory amplitude $\beta$. The wavelength W of the rays 14 reaching the photodetector 6 is thereby modulated by a wavelength amplitude $\delta W$.

The diffraction grating 11 advantageously reflects the diffracted incident radiation 2 asymmetrically in a predetermined diffraction order to achieve maximum intensity and dispersion of the rays 14. The diffraction grating 11 itself preferably has focusing capabilities so that the mirrors 8 and 9 or only the focusing mirror 9 can be dispensed with in order to avoid reflection losses.

Small single-crystal silicon wafers with etched grating structures according to EP-A 387 407 can be used advantageously as the diffraction grating 11. Typically, such small silicon wafers have a surface area of 3 cm² and a thickness of 0.2 mm, have little mass, and are not significantly deformed by accelerations due to the rotational and oscillatory movements.

Advantageously, the driving means 16 comprises a galvanometer whose core-free coil has very little inertia and whose axis 10 is preferably mounted in jewel bearings (e.g., ruby bearings) in order to minimize bearing friction. This driving means 16 advantageously converts a drive signal in a linear fashion into an angle of rotation $\Theta$ and is also able to transfer the rotational movement with the rapid superimposed oscillatory movement to the axis 10. The angle of rotation $\Theta$ of the galvanometer which is limited to approximately 90° suffices for use in the monochromator 5. The diffraction grating 11 can also be set to a predetermined wavelength W which is modulated by the wavelength amplitude $\delta W$ by means of this driving means 16.

In addition to the monochromator 5 located in the housing 17, the spectrophotometer also comprises an electronic unit 18 which feeds the drive signal to the driving means 16 and evaluates the measuring signal from the photodetector 6. The construction of unit 18 depends to a great extent on the design of the monochromator 5.

Unit 18 may, for instance, contain an evaluating circuit 19 with a display device 20 and a control circuit comprising a drive generator 21, a modulation generator 22, and a mixing-amplifier 23.

An output of the modulation generator 22 is connected to a first input 24 of the mixing-amplifier 23 as well as to a synchronization input 25 of the evaluation circuit 19. The modulation generator 22 produces a modulation signal (e.g., sinusoidal, rectangular, etc.), the frequency $f_1$ and amplitude of which can be set in advance.

A first output of the drive generator 21 is connected to a second input 26 of the mixing-amplifier 23. A clock signal line 27 connects a second output of the drive generator 21 and a clock input 28 of the display unit 20 to transmit a clock signal. The drive generator 21 produces a rotation signal at its first output to control the rotational movement of the driving means 16, e.g., a rising asymmetric saw-tooth voltage with a frequency $f_2$ and with a predetermined amplitude. The clock signal line 27 directs the clock signal to the display unit 20 for synchronization at the beginning of each period of the rotation signal.

An output of the mixing-amplifier 23 is connected via a supply line 29 to the driving means 16. The mixing-amplifier 23 superimposes the modulation signal appearing at the first input 24 onto the rotation signal arriving at the second input 26. The rotation signal modulated with the modulation signal is amplified in a predetermined linear manner and is supplied to the driving means 16 as a drive signal.

Depending on the kind of the photodetector 6, the superimposed modulation signal may have, for example, a frequency $f_1$ in the range of 5 to 10 Hz for the oscillatory movement while the rotation signal has a frequency $f_2$ between 1 mHz and 10 mHz. The amplitudes of the two signals are selected in such a manner that the galvanometer executes oscillations with an oscillatory amplitude $\beta$ of 0.2° to 2° and a rotational movement $\Theta$ in the range of 40° to 60° under the effect of the drive signal. The parameters $f_1$, $f_2$, $\beta$ and $\Theta$ are adjustable and are preselected for the spectrophotometer, e.g., an angle of rotation $\Theta < 40°$ and a frequency $f_2 > 10$ mHz can be selected if appropriate.

The measuring signal at the photodetector 6 is brought via a signal line 30 to a signal input 31 of the evaluation unit 19. An output of the evaluation unit 19 is connected to an input of the display unit 20 via a display line 32.

The working principle of the spectrophotometer can be used over the entire spectrum of the radiation 2, from ultra-violet to long-wave infrared. If the testing procedure is limited to only a predetermined portion of the spectrum, e.g., to a wavelength in the range between 1 and 10 $\mu m$, the spectrophotometer can be produced in a small size and at low cost. The input opening 4 is preferably separated from the testing chamber 3 by a single transparent window 33 (which may be made of, e.g., Si, Ge or $CaF_2$).

Figure 2:
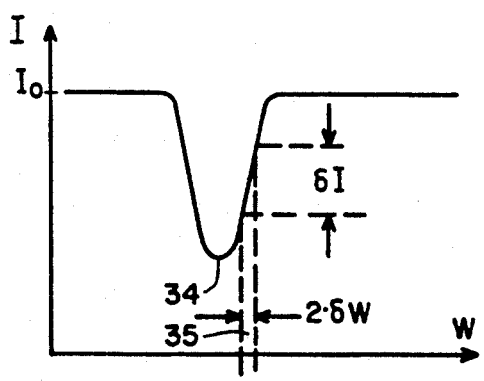
FIG. 2 shows a spectrum with an absorption band.

FIG. 2 shows a typical section of an absorption spectrum in which the intensity I of the radiation 2 is plotted as a function of the wavelength W. The radiation 2 is emitted from the light source 1 at a constant spectral intensity $I_0$ in the graph shown. A substance traversed by the radiation 2 in the testing chamber 3 causes a lowering of the intensity $I_0$ by reason of its absorption for at least one characteristic wavelength, and after reaching a minimum 34, the depth of which depends on the quantity of the irradiated substance, the intensity returns to its original level $I_0$.

Due to the combined rotational movement and oscillatory motion of the diffraction grating, the wavelength W is shifted by the predetermined wavelength amplitude $\delta W$, which gives rise to an analysis range 35 of width $2\delta W$, the shift being in the direction of increasing wavelength W across the spectrum shown in FIG. 2. The modulation of the wavelength W by amplitude $\delta W$ causes a change $\delta I$ in the intensity I(W) within the range of absorption of the substance. The size of $\delta I$ is proportional to the slope of the intensity function I(W).

If the analysis range 35 is in the area of constant intensity $I_0$, i.e., outside the absorption range of the substance, the photodetector 6 produces a constant measuring signal $S_o$, i.e., it does not change as a result of the wavelength modulation through the oscillatory motion.

If the intensity I(W) decreases in the analysis range 35, the measuring signal produced at the photodetector 6 is made up of a direct-current component and an alternating-current component with a frequency $f_1$ corresponding to the oscillatory motion, the oscillatory motion and the measuring signal being out of phase by 180° in the case when the oscillation is in its first quadrant in the direction of increasing wavelength W. If the intensity I(W) increases in the analysis range 35, the oscillating motion and the measuring signal are in phase.

The evaluation circuit 19 (FIG. 1) amplifies only the a.c. portion of the measuring signal so that the d.c. component, which is great when absorption occurs, is effectively suppressed. An output signal of the evaluation unit 19 is obtained from the synchronization to the modulation signal of the a.c. component of the measuring signal whereby each half-wave of the measuring signal is connected to form the output signal with the sign determined by the phase difference between the amplified measuring signal and the modulation signal which is introduced directly at the synchronization input 25 of the evaluation circuit 19. The output signal is proportional to the slope of the function I(W). A circuit that can be used for the evaluation circuit 19 is known as a lock-in amplifier. In the display unit 20 (FIG. 1), the integrated output signal of the evaluation circuit 19 can represent, for instance, the intensity I(W) directly on a screen in the form shown in FIG. 2, whereby it is possible for the display signals obtained during successive rotational movements to be synchronized with the pulses.

The spectrophotometer according to the present invention has a number of advantages over prior art devices, such as simple construction, a testing chamber 3 that can be of practically any desired size, low-cost, low-noise amplification of the measuring signal thanks to the modulation of the wavelength W, and the ability to measure absorption as well as emission of light by the irradiated substances.

The resolution of the spectrophotometer ranges from 50 to 100 waves per cm within a spectral range of 0.8 to 10 $\mu$m, which is sufficient to detect pollutants such as $CO_2$, $SO_2$, $NH_3$, etc. The wavelength amplitude $\delta W = 0.17$ $\mu$m is suitable to detect $CO_2$, for example. The minimum 34 of the $CO_2$ absorption lies in the region of about 4.2 $\mu$m.

Figure 3:
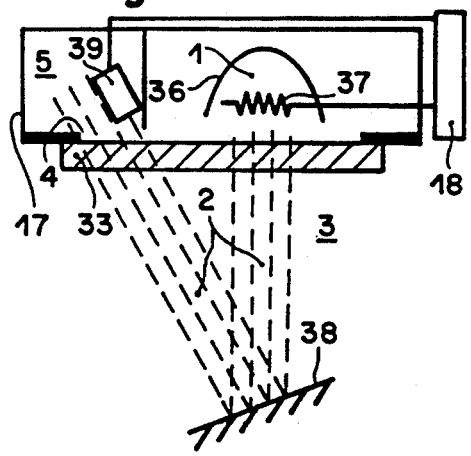
FIG. 3 shows a light source with a heating coil.

The light source 1 is shown in greater detail in FIG. 3. The light source 1 is provided with a filament 37 at the focal point of a parabolic mirror 36. If wavelengths W > 1 $\mu$m are to be produced, the filament 37 can be exposed directly to the atmosphere of the testing chamber 3 so that no glass bulb surrounding said filament 37, which could result in absorption losses of the radiation 2, will be required. The light source 1 can also be installed within the housing 17 for the protection of the filament 37 so that the radiation 2 enters the testing chamber 3 after passing through window 33. At least one mirror surface 38 reflects the radiation 2 before it passes through the window 33 once again into the input opening 4 of the monochromator 5. Advantageously, the volume of the testing chamber 3 is taken into account during the testing procedure. Part of the radiation 2 falls in this case on a detector 39 which is located in the housing 17 behind window 33, next to the inlet opening 4. The detector 39 measures the intensity of the radiation 2 and transmits the result to the electronic unit 18. A circuit, not shown here, in the electronic unit 18 regulates the current in the filament 37 and thereby the intensity of the radiation 2.

In FIG. 4, the driving means 16 is shown as comprising a stepping motor which imparts the combined rotational and oscillatory motion to the axis 10 when driven in step at a high number of steps e.g., 1200 steps per 360°. Advantageously, the rotational movement is not limited by the driving means 16 so that the monochromator 5 (FIG. 1) may also function in a different spectral range with great resolution capacity if at least one additional diffraction structure is placed on the back 40 of the diffraction grating 11.

FIG. 5 shows a U-shaped suspension device 41 to which, advantageously, the diffraction grating 11 is mounted by means of two suspension strips 42 connected to the two legs of the suspension device 41 in such manner as to be capable of friction-free swiveling. The suspension strips 42 define the axis 10. Preferably, the suspension strips 42 are connected to a sheet 43 on which the diffraction grating 11 is mounted, e.g., by bonding. Each deflection of the sheet 43 from a rest position produces a restoring force by the suspension strips 42 that is proportional to the extent of the deflection. The suspension strips 42 and the sheet 43 are preferably made of a magnetic glass. The suspension device 41 is located on a plate 44 capable of pivoting around the axis 10. The driving means 16 (FIG. 1) drives the plate 44 at a constant speed whereby a rotation transmitter 45 supplies the clock signals to the clock signal input 28 (see FIG. 1). At least one solenoid is installed on the plate 44, the coils 46 of said solenoid being connected via a galvanic or inductive coupling to the modulation generator 22. The magnetic sheet 43 swivels within the field of coils 46. This arrangement has the advantage that the mixing-amplifier 23 can be omitted.

If the sheet 43 is not a permanent magnet, or if the modulation signal is not superimosable on a d.c. component, the deflection of sheet 43 occurs with twice the frequency of the modulation signal transmitted to the coils 46. The modulation generator 22 transmits a modulation signal to the coils 46 at a frequency $f_1/2$ while the synchronization input 25 receives the frequency $f_1$.

The suspension device 41 is advantageously produced by the methods normally used in micro-mechanics (see, e.g., A. Heuberger, "Micromechanik," Springer Verlag, Berlin 1989, ISBN 3-540-187219). A semiconductor substrate 47 shown in FIG. 6 is provided with a depression 48 in which the sheet 43 together with the diffraction grating 11 is suspended on the suspension strips 42 so as to be able to rotate freely. The substrate 47 is installed on the plate 44 which carries out the pivoting movement around axis 10. Electrostatic or magnetic forces acting between the sheet 43 and the substrate 47 are able to produce the oscillating motion.

The structure may be produced by covering one surface of the substrate 47, which is made of a monocrystalline silicon, with a layer 49 made from a magnetic alloy. Masks (not shown) are used to keep free from the suspension strips 42 and sheet 43 the uncovered areas of the depression 48 of the layer 49. Following the etching process, the suspension strips 42 and the sheet 43 are etched free and are freely rotatable by several degrees around the pivot axis 10. This is sufficient for superimposing the oscillatory motion. Several such substrates 47 can be produced at the same time and can be separated from each other after being produced.

Etching can be carried out on the side of substrate 47 which is not covered by layer 49 in a manner so that the part of the substrate 47 in the area of sheet 43 is provided in one operation a surface structure suitable for the diffraction grating 11, and so that the diffraction grating 11 and the sheet 43 are optimally combined with each other without any additional agent.

Silicon dioxide can also be used for the suspension strips 42 and the plate 43, whereby the plate 43 is provided with at least one additional layer (not shown) of an electrically or magnetically conductive material depending on the selected force between the plate 43 and the substrate 47.

FIG. 7 shows another embodiment of the invention wherein the light source 1 is located outside housing 17 and in the testing chamber 3 itself. The radiation 2, after being reflected from a mirror surface 38, passes through the inlet opening 4 into the monochromator 5 which, in this embodiment, is in the form of Fabry-Perot resonator 50. The Fabry-Perot resonator 50 has an optical length L that can be changed electrically by the driving means 16 in the manner taught by GB 2 818 536A and, depending on its optical length L, filters light of wavelength W from the radiation 2. The Fabry-Perot resonator 50 can be used advantageously as a monochromator 5 since the driving means 16, e.g., a piezo-electric or magnetic means, can be made easily and with low inertia. The focusing mirror 9 intercepts the filtered light rays 14 of wavelength W and projects them onto the photodetector 6.

The optical length L varies with the drive signal modulated with frequency $f_1$ and transmitted over drive line 29 by the mixing-amplifier 23 so that the rays 14 of the wavelength W scan the analysis range 35 (FIG. 2) at the frequency $f_1$ while the analysis range 35 goes through the spectrum of the light source 1 at the frequency $f_2$.

Advantageously, the electronic unit 18 of the device regulates the current going through the filament 37 (FIG. 3) and thereby the intensity of the radiation 2. Furthermore, the electronic unit is also provided with a supply current modulator 51, the inputs of which are connected to the signal line 30 and to the display line 32, and the output of which supplies the light source 1 via a supply line 52. The advantage of this arrangement is that the measurements can be corrected from deviations caused by, for example, influences produced by dirt on the surface irradiated by radiation 2 and by aging of the filament 37 and the photodetector 6.

The supply current modulator 51 comprises a synchronization amplifier 53 (lock-in amplifier) and an a.c. generator 54 which produces an alternating current for the filament 37 at a predetermined supply frequency $f_3$. The supply frequency $f_3$ and the oscillation frequency $f_1$ differ by more than four times and is selected so as to be below the limit frequency for the production of the radiation 2 and below the limit frequency of the photodetector 6. The radiation 2 and the output signal of the photodetector 6 are modulated at a supply frequency $f_3$, preferably 100%. In one example, the frequencies are: for the oscillation signal $f_1 = 9$ Hz, for the rotational signal $f_2 = 1$ mHz, and for the alternating current $f_3 = 37$ Hz.

The lock-in amplifier 53 is set to the supply frequency $f_3$ and amplifies the output signal of the photodetector 6 into a regulating signal for the a.c. generator 54 in order to regulate the current of the filament 37. Because the needed regulating speed is low, the modulation of the regulating signal takes place only during the time when the signal on the display line 32 is within a predetermined range, e.g., when the analysis range 35 (FIG. 2) is in the zone with the unchanged intensity $I_o$.

While the invention has been described by reference to specific embodiments, this was for illustration only. Numerous alternative embodiments will be apparent to those skilled in the art and are considered to be within the spirit and the scope of the invention.

I claim:

1. A spectrophotometer useful for measuring absorption or emission bands of a substance irradiated with optical radiation, comprising a source of optical radiation, a monochromator receiving said optical radiation and including wavelength-determining means for isolating light of wavelength (W) from said optical radiation, electronic control means connected to said wavelength-determining means for supplying an electronic control signal to said wavelength-determining means, said electronic control signal including a first component which causes said wavelength-determining means to scan across a portion of the spectrum of said optical radiation at a frequency ($f_2$), said electronic control means including modulation generator means for generating a second component of said electronic control signal which causes said wavelength-determining means to modulate said light of wavelength (W) by a wavelength amplitude ($\delta W$) at a frequency ($f_1$), photodetection means for detecting the intensity of light isolated by said monochromator and for generating a measuring signal in response thereto, said measuring signal including an a.c. component attributable to said wavelength modulation, and evaluating means for receiving and evaluating said measuring signal, said evaluating means including means for amplifying said a.c. component of said measuring signal in synchronization with said second component of said electronic control signal produced by said modulation generator means.

2. The spectrophotometer of claim 1 wherein said monochromator comprises a diffraction grating rotatable about a pivot axis, the lines of said grating being parallel to said pivot axis, and wherein said wavelength-determining means includes drive means connected to said electronic control means for causing said diffraction grating to rotate about said pivot axis thereby to scan across said portion of the spectrum and for superimposing an oscillatory motion on said rotational movement of said diffraction grating thereby to produce said wavelength modulation.

3. The spectrophotometer of claim 2 further comprising a suspension device for said diffraction grating, said suspension device comprising a sheet for supporting said diffraction grating and suspension strips projecting from said diffraction grating in parallel with said pivot axis by means of which said diffraction grating and said sheet are mounted on said suspension device, said drive means causing said diffraction grating to rotate about said pivot axis by an angle of rotation while said suspension strips apply a restoring force to said diffraction grating which is proportional to said angle of rotation.

4. The spectrophotometer of claim 3 wherein said drive means includes means for generating an electric or a magnetic force which acts upon said sheet.

5. The spectrophotometer of claim 2 wherein said drive means produces said rotational movement and said superimposed oscillatory motion simultaneously.

6. The spectrophotometer of claim 3 further comprising a plate on which said suspension device is mounted, said plate being pivotable about said pivot axis for producing said rotational movement of said diffraction grating, and wherein said drive means further comprises coils disposed adjacent to said sheet for generating a magnetic field which acts on said sheet for producing said oscillatory motion in synchronization with said second component produced by said modulation generator means.

7. The spectrophotometer of claim 6 wherein said drive means causes said plate to rotate about said pivot axis at a constant angular velocity, and wherein said monochromator comprises two separate diffraction gratings which operate one after the other as said plate rotates.

8. The spectrophotometer of claim 3 wherein said suspension device is formed in an etched substrate.

9. The spectrophotometer of claim 1 wherein said monochromator comprises a Fabry-Perot resonator having an optical length, and drive means for adjusting the optical length of said Fabry-Perot resonator, said drive means being connected to said modulation generator means so as to produce said wavelength modulation.

10. The spectrophotometer of claim 1 further comprising a testing chamber containing said substance to be tested, said testing chamber being located between said light source and an inlet opening of said monochromator.

11. The spectrophotometer of claim 10 wherein said testing chamber includes at least one mirror surface to reflect said optical radiation before it enters said monochromator.

12. The spectrophotometer of claim 11 wherein said light source and said monochromator are located within a housing while said testing chamber is located outside said housing, said housing including a window which protects said light source and said monochromator from harmful substances in said testing chamber.

13. The spectrophotometer of claim 1 further comprising supply current modulator means for controlling said light source, said supply current modulator means including synchronization amplifier means connected to said photodetection means for amplifying an output signal of said photodetection means, and a.c. generating means for receiving said amplified output signal from said synchronization amplifier means and for supplying an alternating current at a supply frequency ($f_3$) to said light source, said supply frequency ($f_3$) and said frequency ($f_1$) differ by more than a factor of four.

* * * * *